United States Patent [19]

Lustig

[11] 4,259,069

[45] Mar. 31, 1981

[54] HAND TOOL FOR FINISHING DENTAL FILLINGS

[75] Inventor: Leopold P. Lustig, Newton Centre, Mass.

[73] Assignee: Brasseler, Fed. Rep. of Germany

[21] Appl. No.: 964,974

[22] Filed: Nov. 30, 1978

[51] Int. Cl.$^3$ .............................................. A61C 3/02
[52] U.S. Cl. .................................................. 433/144
[58] Field of Search ................ 32/40 R, 46, 50, 58; 76/DIG. 11; 51/DIG. 26; 433/144, 143; 75/174

[56] References Cited

U.S. PATENT DOCUMENTS

| | | | |
|---|---|---|---|
| 940,351 | 11/1909 | Neugebauer | 32/46 |
| 1,410,296 | 3/1922 | Hannah | 32/40 R |
| 1,455,374 | 5/1923 | Ziesel | 433/144 |
| 1,605,322 | 11/1926 | Bates | 32/46 |
| 2,002,245 | 5/1935 | McDaniel | 32/46 |
| 2,334,755 | 11/1943 | Eglintion | 76/DIG. 11 |
| 2,366,671 | 1/1945 | Montelius | 433/144 |
| 2,634,499 | 4/1953 | Bowes | 30/317 |
| 3,725,055 | 4/1973 | Rudy | 75/174 |
| 4,060,897 | 12/1977 | Greinstein | 32/46 |

*Primary Examiner*—Gene Mancene
*Assistant Examiner*—John J. Wilson
*Attorney, Agent, or Firm*—Wolf, Greenfield & Sacks

[57] ABSTRACT

The hand tool is used as a cosmetic dental trimmer for restorative material of the composite resin type to remove any excess of such material to more perfectly contour the restorative material to match the natural contour of the original tooth surface. The tool includes an elongated handle connected by a tapering shank to the trimming (shaving) blade which has a hard metal layer, such as tunsten carbide, having the property that it will not discolor the composite resin material. The blade is preferably formed, in one embodiment, by a very slightly concaved face defining the blade along an arcuate (concave) edge thereof. Preferably, a pair of tools are used with oppositely arranged blades. Alternate embodiments include a tool having an excavator blade and one constructed as a composite shaver or shaper.

4 Claims, 11 Drawing Figures

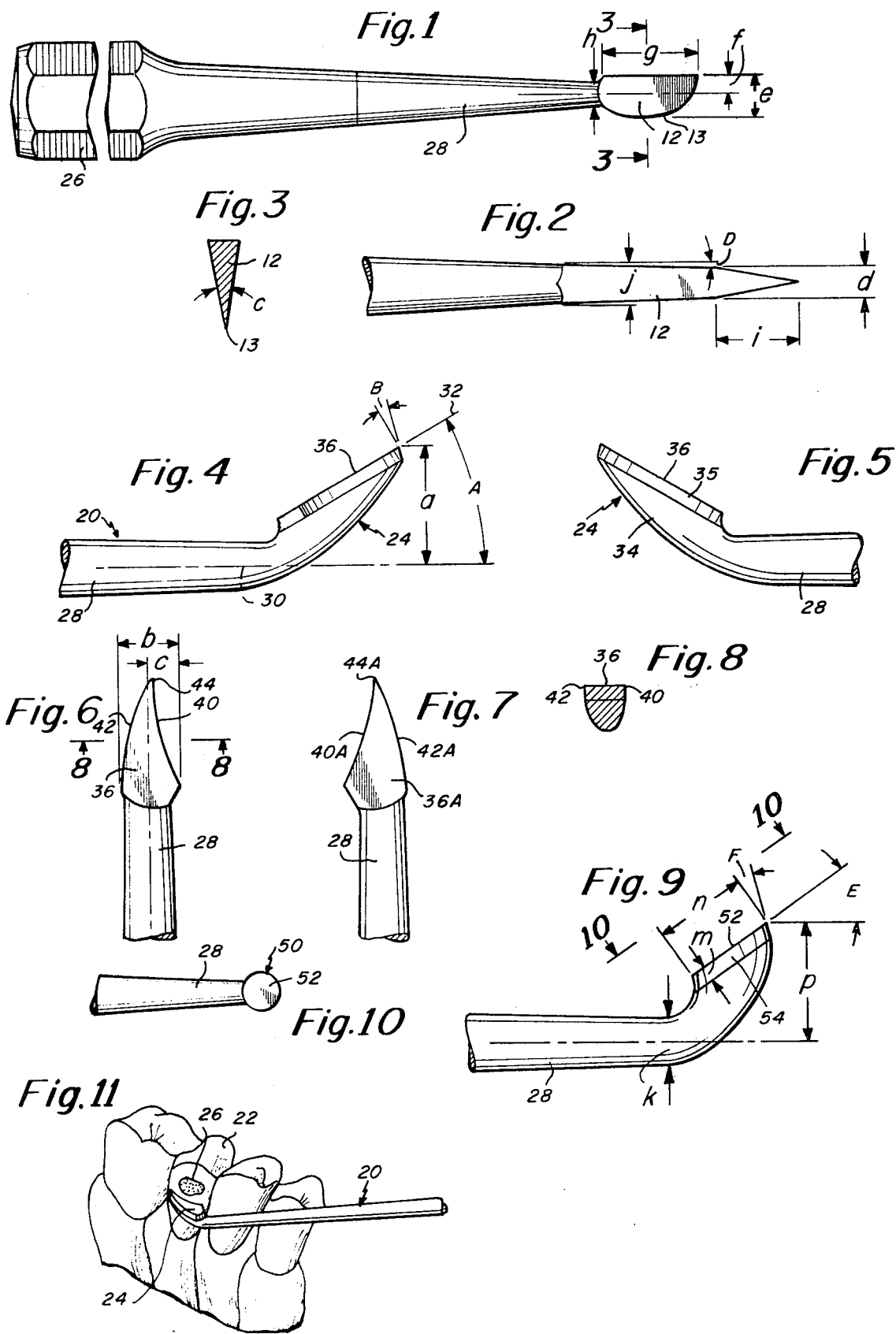

HAND TOOL FOR FINISHING DENTAL FILLINGS

BACKGROUND OF THE INVENTION

The present invention relates in general to a dental hand tool used for trimming restorative material which is used as a filling in dental work. The tool of this invention is particularly adapted for use for trimming more modern filling material such as composite resin dental materials. The trimming tool of this invention is for removing excess restorative material so as to more perfectly contour the restorative material to match the natural crown or contour of the original surface. The trimming in accordance with the invention is accomplished by a novel shaving blade construction, preferably of a hardened material, such as tungsten carbide, which avoids the staining of more modern filling materials such as composite resin restorative materials.

In restorative dentistry, especially when using cosmetic (white) filling or crown material, the trimming step is performed so as to preserve and enhance the cosmetic appearance of the restoration. Typically, this step involves removing excess restorative material so that there is a smooth matching contour between the restorative material in the filled cavity and the original tooth surface. Also, it is important to have a smooth transition between the tooth surface and the restorative material without the presence of any abrupt joint.

A common technique for shaping the restorative material involves the use of a rotary instrument such as a rotary burr which essentially grinds the hardened restorative material by an abrasive action. However, this technique is dangerous because there is a chance of destroying the hard tooth substance. Also, the composite resin dental restorative material sets to a hardened shatterable state, so that it is like glass and somewhat brittle and, therefore, the vibration caused by the use of a burr instrument may cause small fragments of the material to shatter particularly at the margins, thus creating small voids. In consequence, as is known, vibration from a burr or other rotary tool can cause iatrogenic damage. These small voids or cracks are a problem as they may be an annoyance to the patient, and also can fill with plaque or other undesirable substances which can damage the host tooth and shorten the life of the restoration.

Existing dental instruments do not use a carbide tip. Carbide has been employed primarily in constructing chisels and the like instruments, where hardness is required but this material has not been used in construction of dental hand-tools used in dental restoration for the shaping of restorative material. However, it is an object of this invention to provide a dental trimmer having at least the blade edge of a hardened material such as tungsten carbide. This material is also advantageous in that it prevents staining of the restorative material. If the restorative material is of a cosmetic nature such as the composite resins with which this invention is concerned, the tool that is used should not stain or otherwise contaminate the filling material. Generally, this rules out tools that are constructed of ferrous material.

The following prior art patents show bladed instruments: U.S. Pat. Nos. 940,351; 1,605,322; 2,634,499; and 4,060,897. The Bates U.S. Pat. No. 1,605,322 shows a pyorrhea curette which is more of a surgical instrument for cutting soft tissue or cleaning out debris and granulation tissue. This instrument is not adapted especially in its shape for contouring restorative material used in dental restoration. This prior art instrument is primarily for use beneath the gum line whereas the instrument in accordance with the present invention is primarily for use above the gum line.

The Greenstein U.S. Pat. No. 4,060,897 is not an instrument that is for use in the mouth but is used in making a dental restoration by a vibration technique where the restoration is to be fired in an oven and is primarily constructed of a ceramic porcelain. Furthermore, the structure shown in this prior art patent again is not adapted especially in its configuration for use in shaving restorative material which is used as a filling in an existing tooth surface.

SUMMARY OF THE INVENTION

In accordance with the present invention there is provided a hand tool for finishing contours of dental fillings made of composite resin restorative materials, which materials are susceptible of being stained by ferrous materials. The tool of this invention is preferably for trimming restorative material to remove any excess of such material so as to more perfectly contour the restorative material to match the natural contour of the original tooth surface. The blade of the hand tool in accordance with the invention has a hard metal layer such as one of tungsten carbide having the property that it will not discolor the composite resin material. The hard metal blade has at least one edge which is shaped to match a natural contour of a selective portion of a tooth for shaping fillings made of such resin material while avoiding upsetting the cosmetic coloration of a restoration. In accordance with the invention the tool may comprise a blade member which is preferably integrally connected with a handle by means of a forearm that is tapered from the wider handle to the relatively small blade member. In accordance with one embodiment of the invention the blade or shaving member extends at an angle to the longitudinal axis of the handle and preferably has a slightly concaved face which also extends at an angle to the longitudinal axis of the handle. In this embodiment the face of the blade member has a surrounding edge including a sharpened blade edge extending along one side of the face. This sharpened blade edge has a slightly concavely-arcuate contour so as to match the natural convexly-arched crown of the tooth contour. In this embodiment the face has another opposite edge that is convexly curved and this is preferably not sharpened. The arcuate curvature on the sharpened edge is preferably a concave curvature. The concavely and convexly curved edges on the face preferably converge and terminate at a pointed tip. In an alternate embodiment of the invention the blade member is in the form of an excavator having a substantially flat circular or elliptical face but also provided with a hard metal layer having the property that it will not discolor the composite resin material. Still a further embodiment of the invention discloses a composite blade or shaping member also having a hardened metal portion thereof.

BRIEF DESCRIPTION OF THE DRAWINGS

FIG. 1 is an elevation view of a composite shaving or trimming device in accordance with the invention;

FIG. 2 is a fragmentary view showing further detail of the blade of the member of FIG. 1;

FIG. 3 is a cross-sectional view taken along line 3—3 of FIG. 1;

FIG. 4 is an elevation view of another embodiment of the present invention;

FIG. 5 is an elevation view showing the tool of FIG. 4 from the opposite direction;

FIG. 6 is an orthogonal view toward the face of the tool of FIG. 4;

FIG. 7 is a view similar to the one shown in FIG. 6 for a tool having a curvature in the opposite direction;

FIG. 8 is a cross-sectional view taken along line 8—8 of FIG. 6;

FIG. 9 shows still another embodiment of the present invention;

FIG. 10 is a cross-sectional view taken along line 10—10 of FIG. 9 directed at the face of this device; and FIG. 11 shows a tool of this invention such as the one depicted in FIG. 4 in use for contouring a filling.

DETAILED DESCRIPTION

Referring now to the drawings, there is shown a dental hand tool in accordance with the present invention which is employed as a tool for shaving or trimming dental restorative material preferably of the composite resin type to remove excess material which has previously been compressed to form a filling. This material is removed by a shaving or trimming action so as to more perfectly contour the restorative material to match the natural contour of the original tooth surface. FIG. 11 shows the hand tool 20 of FIG. 4 in position in the patient's mouth on the tooth surface of tooth 22 which is one of the four teeth illustratively shown in FIG. 11. The blade member 24 of the hand tool of this embodiment is depicted contacting the tooth surface about to be swept upwardly to shave the restorative material 26 forming a filling in the tooth 22. The tool of this invention is primarily adapted for the finishing or restorative material of the composite resin type and is not well adapted for contouring an amalgam such as used in gold or silver fillings.

The dental hand tool 20 comprises, in addition to the blade member 24, an elongated handle 26 of circular or octogonal cross section integral with a tapering forearm 28 which is also integrally contiguous with the blade member 24. The blade member 24 extends angularly to the longitudinal axis 30 of the handle and forearm. FIG. 4 depicts an angle A between the axis 30 and the general center line 32 of the blade member 24. The angle A is an acute angle preferably on the order of 30°. The blade member 24 comprises a base portion 34 and a top portion 35 defining the face 36. The face 36 is planar but may also be slightly concave with a slight radius curvature. The length 1 of the face 36 may be on the order of 3 millimeters. The embodiment of FIG. 11 is substantially the same as the one of FIG. 4 except for the slight concave of the face 36.

As depicted in FIG. 6, the face 36 is primarily defined by a sharpened blade edge 40 having a concave radius of curvature S. The length of the edge 40, as depicted in FIG. 6, may be on the order of 1.5 millimeters while the radius of curvature S may be on the order of 6 centimeters. The sharpened edge 40 is the principal shaving edge and in a preferred embodiment is constructed of a hard tungsten carbide material. The face 36 is also partially defined by another opposite convexly curved edge 42 that, in a preferred embodiment, is left unsharpened. Edge 42 may have a radius curvature on the order of 5.5 millimeters. The concavely curved edge 40 and the convexly curved edge 42 converge at a pointed tip 44. It is actually preferred to have the face of a hard metal to a thickness of say 0.3 millimeters. The sharpened blade edge 40 is also depicted in FIG. 11 and is preferably constructed with a radius of curvature S that closely matches the curvature of substantial portions of the teeth, such as tooth 22 shown in FIG. 11. In an alternate embodiment the curvature may be more pronounced than shown in FIG. 6 for a tool that is to be used more in between the teeth or about abrupt changes in curvature of the teeth. However, a curvature as depicted in FIG. 6 has been found quite useful with virtually all surfaces of the teeth.

In the embodiment of FIG. 4 other dimensions illustrated on the drawing are a=2.5 millimeters, b=1.4 millimeters and c=0.9 millimeters.

FIG. 7 shows a complementary embodiment to the one shown in FIGS. 4-6. In this embodiment there is also shown the curved edges 40A and 42A terminating in tip 44A. However, in this version the shaving edge 40A is facing in the opposite direction to the edge 40 showin in FIG. 6. With regard to the perspective view of FIG. 11 the instrument of FIG. 7 would be usable on the opposite surface of the tooth 22. Thus, it is preferred that a pair of these tools be employed with one or the other being selected depending upon the particular side of the tooth that is being finished. FIG. 11 shows one version of the tool of this invention in use. The length 1 of the face is generally longer than the cross dimension of the filling being contoured, thus permitting portions of the face to rest on the tooth surface stabilizing the tool as it passes to shave the restorative material.

Another embodiment of the present invention is shown in FIGS. 1-3. This embodiment shows a tool having a handle 26, a forearm 28, and a different construction for a blade member identified as blade member 12. This embodiment is referred to as a composite shaver or scraper with the blade member 12 forming a blade edge 13. Again, in this embodiment the edge 13 which will contact the restorative material is made of a hard metal such as a tungsten carbide. In this embodiment the angle C depicted in FIG. 3 may be on the order of 10°. Other important dimensions shown in FIGS. 1-3 are d=0.6 millimeters, e=2.0 millimeters, f=0.5 millimeters, g=5.0 millimeters, h=0.8 millimeters, i=2.0 millimeters and j=0.8 millimeters. Also, it is noted from FIG. 2 that there is a very slight angle D which may be on the order of 1° 30'.

FIGS. 9 and 10 show a further embodiment of the present invention depicting substantially only the blade portion of the instrument. In FIGS. 9 and 10 there is shown a forearm 28 connecting to a blade member indicated as member 50 having a circular face 52. In the area 54 adjacent to the face and partially forming the face there is provided the hard metal such as a tungsten carbide. In certain embodiments herein only the very blade portion has been shown as being made of tungsten carbide or the like. However, it is understood that a larger portion of the blade member could also be constructed of this hard metal or even substantially the entire blade member. In FIGS. 9 and 10 the following dimensions apply k=1.0 millimeters, m=0.4 millimeters, n=2.0 millimeters and p=2.5 millimeters. In addition, the angle E=35° and the angle F=15°.

What is claimed is:

1. A hand tool for finishing crown contours of dental fillings made of composite resin restorative materials which set to a hardened shatterable state, comprising, an elongated handle and a blade member for shaving such restorative material forming the filling, said member connected directly to and contiguous with the handle and extending at an obtuse angle to the longitudinal axis of the handle, said shaving member having a substantially flat face also extending at an obtuse angle to said longitudinal axis, said face having means defining a sharpened blade edge extending along one side of said face, said sharpened blade edge having a slight concaved arcuate contour substantially to match the crown contour of the tooth, and constructed of a hard non-ferrous tungsten carbide material to prevent restorative material discoloration and contamination, said blade edge terminating in a tip displaced away from the center line of the elongated handle by a dimension at least as great as the length of the blade edge, said blade edge having a length comparable to the maximum width of the shaving member face, said shaving member face having a length on the order of three millimeters, said shaving member face also having a length on the order of twice the maximum width thereof, the length of the blade edge also being on the same order as the maximum width of the blade member face.

2. A hand tool as set forth in claim (13) 1 wherein (said) the dimension (a) from the longitudinal axis of the handle to the tip is on the order of 2.5 millimeters.

3. A hand tool as set forth in claim 1 wherein the length of the blade edge is on the order of 1.5 millimeters.

4. A hand tool as set forth in claim 3 wherein said angle is on the order of 30°.

* * * * *